United States Patent [19]

Bosone et al.

[11] Patent Number: 4,474,980

[45] Date of Patent: Oct. 2, 1984

[54] PROCESS FOR THE PREPARATION OF INTERMEDIATES FOR PYRETHROIDS

[75] Inventors: Enrico Bosone, Milan; Franco Gozzo, S. Donato Milanese, both of Italy

[73] Assignee: Montedison S.p.A., Milan, Italy

[21] Appl. No.: 445,414

[22] Filed: Nov. 29, 1982

[30] Foreign Application Priority Data

Dec. 2, 1981 [IT] Italy .............................. 25407 A/81

[51] Int. Cl.³ .......................................... C07C 69/743
[52] U.S. Cl. .................................................. 560/124
[58] Field of Search ........................................ 560/124

[56] References Cited

U.S. PATENT DOCUMENTS

| | | | |
|---|---|---|---|
| 3,998,868 | 12/1976 | Mizutani | 560/124 |
| 4,070,404 | 1/1978 | Lupichuk | 560/124 |
| 4,401,673 | 8/1983 | Martel | 560/124 |

FOREIGN PATENT DOCUMENTS 31041 7/1981 European Pat. Off. ............ 560/124

*Primary Examiner*—Michael Shippen
*Attorney, Agent, or Firm*—Morgan, Finnegan, Pine, Foley & Lee

[57] ABSTRACT

There is described a process for the preparation of 2,2-dimethyl-cyclopropanecarboxylates carrying in position 3 a halosubstituted dienic substituent.

Said compounds are intermediates for the synthesis of pyrethroid insecticides.

8 Claims, No Drawings

PROCESS FOR THE PREPARATION OF INTERMEDIATES FOR PYRETHROIDS

BACKGROUND OF THE INVENTION

In European Pat. Appl. No. 31.041, there are described, amongst others, also certain pyrethroid insecticides falling under the following general formula:

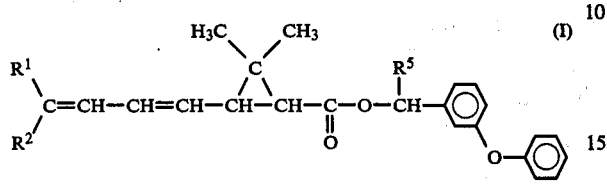

wherein:
$R^1 = F, Cl, Br, CF_3$;
$R^2 = F, Cl, Br$;
$R^5 = H, CN, C\equiv CH$

The preparation of the compounds of formula I is carried out starting from cyclopropanecarboxylates intermediates of formula:

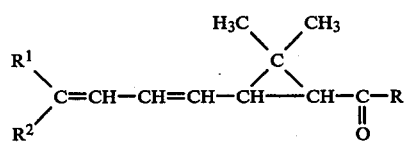

(wherein: $R = OH$, a $C_1-C_4$ alkoxy, a halogen, while $R^1$ and $R^2$ have the meanings given in general formula I).

For the synthesis of the compounds of formula I, the esters of formula II in which $R = $ alkoxy, are hydrolyzed to the corresponding free acids (II, $R = OH$) and converted to the corresponding acyl halides (II, $R = $ halogen), these latter being then condensed with suitable alcohols of the formula:

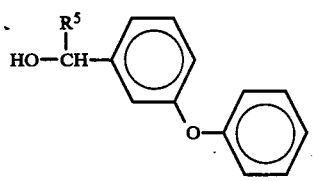

wherein: $R^5 = H, CN, C\equiv CH$.

In above cited European Pat. Appl. there have also been described some processes for the preparation of the intermediates of formula II in which $R = C_1-C_4$ alkoxy, Amongst these processes, for instance, there may be cited the reaction between 1-alkoxycarbonyl-2',2'-dimethyl-cyclopropylmethyl-triphenylphosphonium bromide and a halosubstituted acrylic aldehyde, and the reaction between a haloallylphosphonate and caronaldehyde.

THE PRESENT INVENTION

We have now found a process for the preparation of the cyclopropanecarboxylates of formula II in which $R = $ alkoxy having from 1 to 4 carbon atoms.

The process, object of this invention, consists of a plurality of steps which will be described in the following.

The fist step consists in the addition of an alkyl halide (tetrahalomethane or hexahaloethane) of formula:

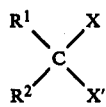

(A)

[wherein $R^1 = F, Cl, Br, CF_3$; $R^2 = F, Cl, Br$; X and X' (either equal to or different from each other) = Cl, Br] to the compound 4-hydroxy-5-methyl-hexene-1 of formula

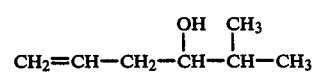

(B)

This reaction gives compounds of formula:

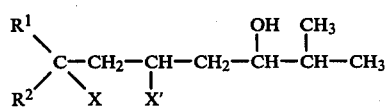

(C)

which, in the second step of the process, are dehydrated thereby yielding the alkenes of formula:

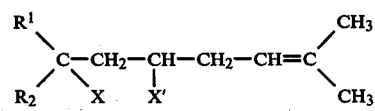

(D)

In the third step of the process, the alkenes of formula (D) are made to react with diazoacetate

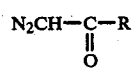

(E)

(wherein: $R = C_1-C_4$ alkoxy), thereby yielding the cyclopropanecarboxylates of formula:

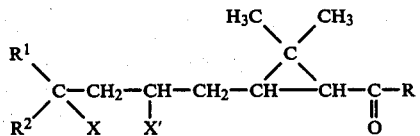

(F)

Finally, the cyclopropanecarboxylates of formula (F) are dehydrohalogenated by treatment with 2 base equivalents (fourth step) thereby yielding the compounds of formula (II) in which $R = $ alkoky with 1-4 carbon atoms.

In compounds C, D, E and F, the symbols $R^1$, $R^2$, X, X' and R, wherever present, have the same meanings indicated above.

The above mentioned reactions are summarized in the following Scheme 1 and will be commented in the following.

SCHEME 1:

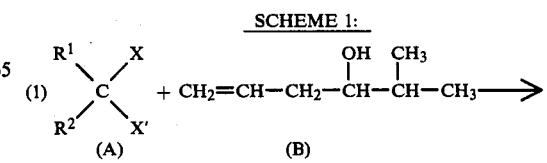

-continued
SCHEME 1:

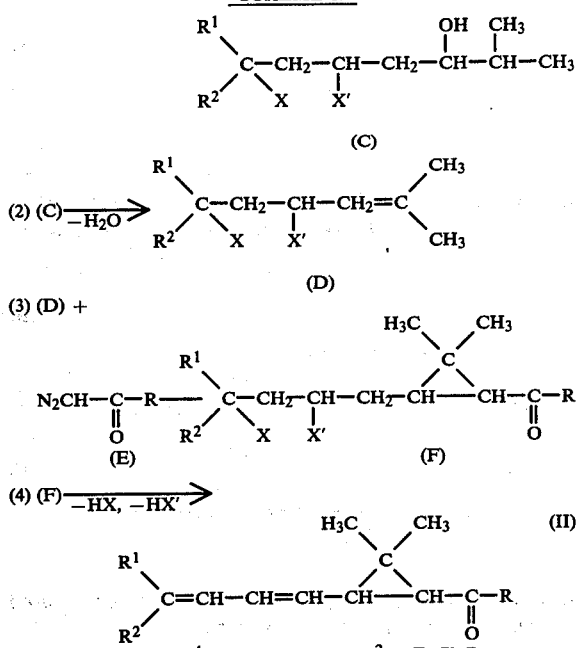

[R = C₁-C₄ alkoxy, R¹ = F, Cl, Br, CF₃; R² = F, Cl, Br; X = Cl, Br; X' = Cl, Br].

1st Step

The reaction between 4-hydroxy-5-methylhexene-1 (compound B) and haloalkane A is carried out in an inert solvent and in the presence of a suitable catalyst. This latter may be a radical reactions promoter, such as for instance organic peroxides or Redox-transfer systems such as copper salts (copper$^I$ and copper$^{II}$) in the presence of aliphatic amines or ethanolamine, iron salts in the presence of alcohols, trialkylphosphites or amines, ruthenium$^{II}$ salts or again iron-pentacarbonyl.

4-hydroxy-5-methyl-hexene-1 is a known compound that may be prepared, for instance, by means of a Grignard reaction between allyl chloride and 2-methylpropanale, according to what described in: "Chemisches Zentralblatt 1942 I 28".

The haloalkanes of formula A are known compounds. Amongst these known compounds there may be listed: CF₃—CFBr₂, CF₃—CFCl₂, CF₃—CCl₃, CF₃—CClBr₂, CCl₄, CBr₄, CF₂Br₂, etc.

2nd Step

For the dehydration of compound C, there may be used known dehydrating agents such as for instance P₂O₅ and strong acids such as for instance concentrated sulphuric acid, p.toluenesulphonic acid, trifluoroacetic acid.

The reaction is carried out in an inert solvent when using P₂O₅ as a dehydrating agent, according to known techniques. On the contrary, when using strong acids, these may also be used without a solvent.

3rd Step

The reaction between diazoacetate and an unsaturated compound, by itself a known reaction, in general is conducted in the presence of copper salts (for instance: CuSO₄) and metal copper finely comminuted.

For the reaction of Step 3 of the process object of the present invention, it has been verified that, besides the above mentioned catalytic system, also other catalytic systems are suited for the purpose, such as for instance palladium or rhodium salts.

With these latter systems the reaction provides higher yields and proceeds at room temperature.

Suitable solvents are, for instance, cyclohexane, dicloroethane or methylene chloride.

4th Step

The dehydrohalogenation reaction of the compounds of formula E, which involves the loss of two mols of halogen-hydric acid (HCl or HBr) per each mol of substrate, is carried out in a polar solvent and in the presence of an at least bimolecular amount of a halogen-hydric acid-accepting base.

A method which yields good results, consists in carrying out the reaction in dimethylformamide at about 100° C. and by using anamine as a base.

Alternatively, the reaction of dehydrogenation may be carried out under milder operational conditions and in two stages.

Thus, for instance, there may be carried out a first dehydrohalogenation by treatment with a base (amine) at room temperature, and by then effecting a second dehydrohalogenation by heating the reaction mass in the presence of Lewis acids.

An alternative procedure in the process object of the present invention, consists in inverting the order of steps 3 and 4.

According to this procedure, the unsaturated intermediate D is dehydrohalogenated in order to yield a triene of formula:

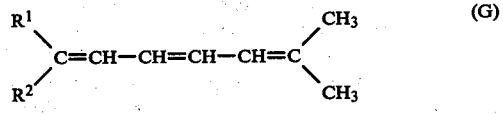

which is then made to react with diazoacetate, according to the reactions reported in the following Scheme 2.

SCHEME 2:

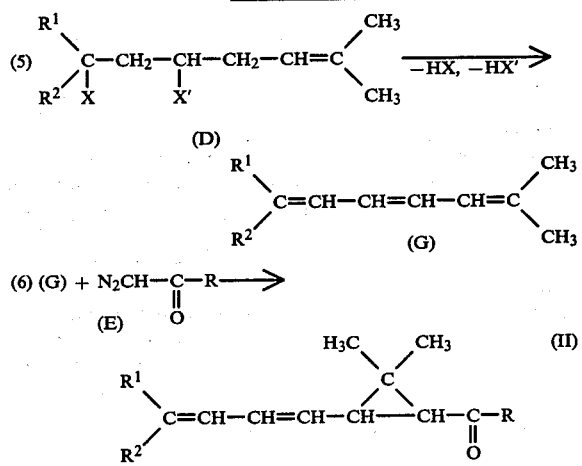

[R, R¹, R², X and X' have the same meanings reported in scheme 1].

Reaction 5 and reaction 6 are carried out according to the procedures reported herein above for the reactions of steps 4 and 3 respectively.

With respect to the processes for synthesis of the compounds of formula II, wherein $R=C_1-C_4$ alkoxy reported in European Patent Appl. No. 31.041, the process of the present invention proves more convenient because it requires starting products that are available or easily accessible and cheaper reactants, besides being in general easier to be executed.

The compounds of formula II are useful, besides as intermediates for the preparation of pyrethroids of formula I, also as precursors of other cyclopropanecarboxylates.

In fact, the dienic system is suitable for various reactions which allow the introduction into the molecule of other groups. In order to better illustrate the invention, there will now be given a series of examples.

EXAMPLE 1

Preparation of compound 7,8,8,8-tetrafluoro-5,7-dibromo-2-methyl-octan-3-ol

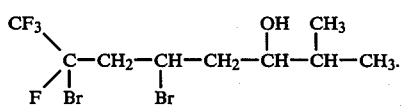

Into a 1 liter flask equipped with a stirrer and a reflux condenser there were introduced:
0.45 mols of

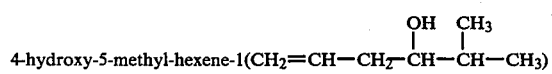
4-hydroxy-5-methyl-hexene-1 (CH$_2$=CH—CH$_2$—CH—CH—CH$_3$)

0.45 mols of 1,1-dibromo-tetrafluoroethane (CF$_3$—CFBr$_2$)
113 mols of ethyleneglycol-dimethylether (diglyma)
0.023 mols of benzoyl peroxide.

The reaction mixture was thereupon reflux-heated (at about 85° C.) for 1 hour, after which it was then cooled down and additioned with:
0.45 mols of 1,1-dibromo-tetrafluoroethane and
0.023 mols of benzoyl peroxide.

The mixture was then again reflux-heated for other 2 hours. After cooling down, the mixture was additioned with 200 ml of methylene chloride (CH$_2$Cl$_2$).

Thereupon it was washed with an aqueous solution of NaHCO$_3$ at a 5% concentration (2×100 ml) and then with a saturated NaCl solution (2×100 ml).

After drying and removal of the solvent by distillation under reduced pressure, there were obtained 200 g of raw product which was then distilled under vacuum, gathering the fraction boiling at between 79° and 82° C. at the pressure of 0.1 mmHg.

Thereby were obtained 85.8 grams of the desired product.

Infra-red spectroscopy (IR): significant bands at 3400, 1285, 1215, 1185, 1235 and at 720 cm$^{-1}$;

$^1$H-NMR (CDCl$_3$, TMS)
δ(ppm): 0.8–1.1 (d, 6H, CH$_3$),
1.4–2.3 (m, 3H, CH(CH$_3$)$_2$+CH—CH$_2$—CH),
2.2 (s, 1H, OH),
2.6–3.2 (m, 2H, CH$_2$—CFBr),
3.55–3.9 (m, 1H, CH—O),
4.4–4.8 (m, 1H, CH—Br).

(In the NMR spectroscopic data reported in the present text, the following abbreviations are used:
s=singlet; d=doublet; t=triplet; q=quadruplet and m=multiplet or unresolved complex signal).

EXAMPLE 2

Preparation of compound 7,8,8,8-tetrafluoro-5,7-dibromo-2-methyl-octene-2

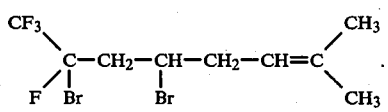

Into a 500 ml flask, fitted with a stirrer and with a dripping funnel, there were introduced 0.17 mols of P$_2$O$_5$ and 170 ml of anhydrous benzene.

To this mixture, kept under stirring at a temperature below 20° C., there were additioned dropwise 0.0835 mols of 7,8,8,8-tetrafluoro-5,7-dibromo-2-methyl-octan-3-ol prepared as described in example 1.

After stirring for 1 hour at room temperature, the mixture was cooled down to about 0° C. and was then additioned dropwise with 100 ml of cold water.

The organic phase was thereupon separated and washed with a 5% NaHCO$_3$ solution (2×100 ml) and with water (2×100 ml).

After drying, the solvent was removed by distillation at reduced pressure thereby obtaining 26.7 g of a raw product which was purified by flashchromatography [Journal of Organical Chemistry 43, 2923 (1978)].

Thereby were obtained 20.8 g of the desired product.

Alternatively, the raw product may be purified by distillation under reduced pressure gathering the fraction that boils at 35°–37° C. at a pressure of 0.05 mmHg.

IR: significant bands at: 1725, 1285, 1215, 1185 and at 720 cm$^{-1}$.

$^1$H-NMR (CDCl$_3$, TMS)
δ(ppm):
1.6–1.85 (s, s, 6H, CH$_3$—C=),
2,5–2.8 (m, 2H, CH$_2$—C=),
2.8–3.1 (m, 2H, CH$_2$—CFBr),
4.2–4.5 (m, 1H, CH—Br),
5.0–5.4 (m, 1H, CH=).

EXAMPLE 3

Preparation of ethyl 2,2-dimethyl-3-(4,5,5,5-tetrafluroro-2,4-dibromopentyl)-cyclopropanecarboxylate

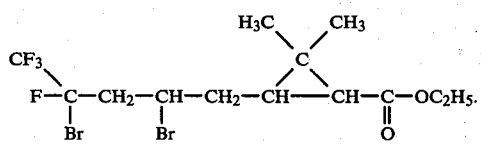

Into a 250 ml flask, fitted with a stirrer and a dripping funnel, there were introduced:
0.1 mols of 7,8,8,8-tetrafluoro-5,7-dibromo-2-methyl-hexene-2 (obtained as described in example 2),
30 ml of 1,2-dichloroethane,
250 mg of Rhodium acetate [Rh$_2$(CH$_3$COO)$_4$].

To this mixture, maintained under stirring at room temperature, a solution of 0.17 mols of ethyl diazoacetate in 30 ml of 1,2-dichloroethane was added dropwise so as to keep the temperature below 25° C.

After about 1.5 hours, once the additioning had been completed, the reaction mixture was washed with water and then dried. The solvent was then removed by evaporation under reduced pressure, thereby obtaining 50 grams of a residue.

After chromatography on silica gel column (eluent: hexane-ethylacetate in the ratio 95:5) there were obtained 33 g of the desidered product.

IR: 1725 cm$^{-1}$ ($\nu$C=O).

EXAMPLE 4

Preparation of ethyl 2,2-dimethyl-3-(4,5,5,5-tetrafluoropenta-1,3-dienyl)-cyclopropanecarboxylate

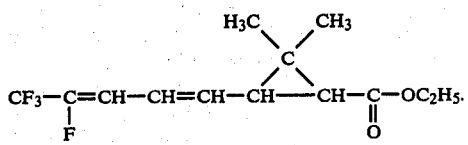

Into a 250 ml flask, anhydrous, and maintained in a nitrogen atmosphere, there were introduced:

10 g (0.023 mols) of the cyclopropanecarboxylate obtained as described in example 3.

7 ml (0.05 mols) of distilled triethylamine, 150 ml of distilled dimethylformamide.

The reaction mixture was maintained under a nitrogen atmosphere and was heated for 24 hours at 100° C. After cooling down, the mixture was then poured into water (300 ml) and extracted with ethyl ether (4×50 ml).

The organic phases, gathered together, were then washed with water (4×50 ml) and dried. The solvent was removed by evaporation at reduced pressure, thereby obtaining 5.6 grams of an oily residue which was purified by chromatography on silica gel (eluent: hexane-ethylacetate in the ratio 95:5).

There were thus obtained 4.5 grams of the desired product.

IR significant bands at: 1725, 1690, 1360, 1200, 1140, 1040, 970 and 710 cm$^{-1}$;

$^{19}$F—NMR (CFCl$_3$+CDCl$_3$)

δ(ppm):

68.5 and 73.5 (CF$_3$), 136 and 137 (F—C=)

$^1$H-NMR (CDCl$_3$, TMS)

δ(ppm):

1.1–1.4 (m, 9H), 1.6–2.3 (m, 2H), 3.95–4.3 (q, 2H), 5.5–6.6 (m, 3H).

EXAMPLE 5

Preparation of the α-cyano-3-phenoxybenzyl ester of 2,2-dimethyl-3-(4,5,5,5-tetrafluoro-pentadienyl)-cyclopropanecarboxylic acid

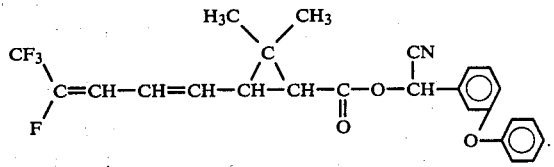

(A) Preparation of 2,2-dimethyl-3-(4,5,5,5-tetrafluoro-pentadienyl)-cyclopropanecarboxylic acid.

The corresponding ethyl ester, prepared as described in example 4, was hydrolized in the presence of a methanolic KOH solution (10%) at reflux temperature for about 2.5 hours. From 1.9 grams of ethyl ester there were thereby obtained 1.46 g of free acid.

IR significant bands at: 3500-2800, 1700, 1640, 1450, 1360, 1200, 1140 and at 710 cm$^{-1}$.

(B) Preparation of the chloride of 2,2-dimethyl-3-(4,5,5,5-tetrafluoro-pentadienyl)-cyclopropanecarboxylic acid.

The product was obtained from the corresponding cyclopropancarboxylic acid (prepared as described under point A) by reaction with SOCl$_2$ in hexane, with yield higher than 95%.

IR significant bands at: 1780, 1690, 1630, 1360, 1200, 1140, 970 and at 770 cm$^{-1}$.

(C) A solution of the acyl chloride obtained as described at point B) (5.75 10$^{-3}$ mols) in 4 ml of anhydrous ethylether was loaded into a 25 ml flask and was then cooled down to about 0° C.

To this solution was then added dropwise a solution of 6.3 10$^{-3}$ mols of α-cyano-3-phenoxybenzyl alcohol in 4 ml of anhydrous ethyl ether.

After 1 hour at room temperature, the mixture was cooled down again to 0° C. and was then additioned, dropwise in a period of 30 minutes, with 5.7 10$^{-3}$ mols of distilled pyridine.

The reaction mixture was then maintained under stirring at room temperature for 15 hours, whereafter it was diluted with ethyl ether, then washed with acid water and with water.

After drying and removal of the solvent, the raw product (2.7 g) was purified by chromatography on silica gel (eluent: hexane-ethylacetate in the ratio 9:1).

Thereby were obtained 2 grams (4.36 10$^{-3}$ mols) of the desired α-cyano-3-phenoxybenzyl ester.

IR significant bands at: 3075, 3060, 1740, 1690, 1630, 1250, 1200, 1130 and at 1070 cm$^{-1}$.

$^{19}$F-NMR (CDCl$_3$+CFCl$_3$),

δ(ppm):

73.5 and 68.5 (CF$_3$), 137 and 136 (F—C=).

EXAMPLE 6

Preparation of 5,7,7,7-tetrachloro-2-methyl-heptan-3-ol $$Cl_3C-CH_2-CH(Cl)-CH_2-CH(OH)-CH(CH_3)-CH_3$$

Into a 250 ml flask equipped with a stirrer and a reflux condenser and kept in a nitrogen atmosphere, there were introduced:

22.8 g of 4-hydroxy-5-methyl-hexene-1, 45 g of carbon tetrachloride, 30 ml of ter-butyl alcohol, 0.2 g of CuCl, 6.1 g of ethanolamine.

The reaction mixture was stirred and reflux-heated (about 83° C.) for two hours.

It was then cooled at room temperature and poured into 100 ml of water. The mixture was made acid with diluted HCl and extracted with methylene-chloride (2×100 ml).

The reunited organic layers were then washed with water till a neutral pH and dried on CaCl$_2$.

The solvent was evaporated at reduced pressure and the residue (50 g) was distilled under vacuum collecting the fraction boiling at 99°–104° C. at 0.25 mmHg.

$^1$H—NMR (CDCl$_3$, TMS)
δ(ppm):
0.97 (d, 6H; geminal methyls),
1.4–2.25 (m, 3H, C$\underline{H}$ (CH$_3$)$_2$+CH—C$\underline{H}_2$—CH),
2.3 (1H, OH),
3.27 (dd, 2H, Cl$_3$C—CH$_2$),
3.5–3.9 (m, 1H, C$\underline{H}$—OH),
4.25–4.8 (m, 1H, C$\underline{H}$—Cl).

EXAMPLE 7

Preparation of 5,7,7,7-tetrachloro-2-methyl-2-heptene $$Cl_3C—CH_2—\underset{Cl}{\underset{|}{CH}}—CH_2—CH=\underset{CH_3}{\underset{|}{C}}—CH_3.$$

Into a 500 ml flask equipped with stirrer, dripping funnel and reflux condenser, there were introduced 12 g of P$_2$O$_5$ in 250 ml of methylene-chloride (CH$_2$Cl$_2$), then dropwise and under stirring, a solution of 10.8 g of 5,7,7,7-tetrachloro-2-methyl-heptan-3-ol (see Example 6) in 50 ml of CH$_2$Cl$_2$.

The reaction mixture was stirred for ten minutes at room temperature then was left to decant.

The methylen-chloride layer was separated. The solvent was removed by evaporation at reduced pressure and the residue (9.9 g) was chromatographed on silica gel (eluent:n-hexane) to yield 7.5 g of the desired product.

$^1$H-NMR (CDCl$_3$, TMS)
δ(ppm):
1.68 and 1.75 (s,s, 6H, geminal methyls),
2.45–2.8 (m, 2H, C$\underline{H}_2$—CH=),
3.2 (d, 2H, Cl$_3$C—C$\underline{H}_2$),
4.05–4.5 (m, 1H, CH—Cl),
5.1–5.45 (m, 1H, CH=).

EXAMPLE 8

Preparation of 2,2-dimethyl-3-(2,4,4,4-tetrachlorobutyl)-cis,trans-cyclopropanecarboxylic acid ethyl ester $$Cl_3C—CH_2—\underset{Cl}{\underset{|}{CH}}—CH_2—CH\overset{\overset{H_3C\diagdown\diagup CH_3}{C}}{\underset{}{\diagup\diagdown}}CH—\underset{O}{\underset{\|}{C}}—OC_2H_5.$$

Into a 500 ml flask equipped with stirrer, reflux condenser and dripping funnel and kept in a nitrogen atmosphere, there were introduced
0.2 g of powdered copper,
0.5 g of anhydrous copper sulphate (CuSO$_4$),
30 ml of dichloroethane (CH$_3$—CHCl$_2$).

To the mixture stirred at reflux temperature, there was added dropwise in about 70 minutes a solution of 5 g of 5,7,7,7-tetrachloro-2-methyl-2-heptene (see Example 7) and 4.5 g of ethyl diazoacetate (N$_2$CH—COOC$_2$H$_5$) in 20 ml of CH$_3$—CHCl$_2$.

The reaction mixture was further reflux heated under stirring for about 10 minutes then it was cooled at room temperature and filtered.

From the filtrate, the solvent was removed at reduced pressure and the residue (9.2 g) was chromatographed on silica gel (eluent n-hexane-ethylacetate in the ratio 95:5).

Thereby were obtained 4.3 g of the desired product (conversion: 64%, yield on converted product: 100%, IR consistent with the assigned structure).

EXAMPLE 9

Preparation of 2,2-dimethyl-3-(4,4-dichlorobutadienyl)-cyclopropanecarboxylic acid ethyl ester $$Cl_2C=CH—CH=CH—CH\overset{\overset{H_3C\diagdown\diagup CH_3}{C}}{\underset{}{\diagup\diagdown}}CH—\underset{O}{\underset{\|}{C}}—OC_2H_5.$$

Into a 250 ml flask equipped with stirrer and reflux condenser and kept in a nitrogen atmosphere, there were introduced:
4.3 g of the cyclopropanecarboxylate obtained as in Example 8,
20 ml of diisopropyl-amine,
100 ml of dimethylformamide.

The reaction mixture was stirred at reflux temperature for 18 hours, then cooled at room temperature and poured into 500 ml of water containing 50 ml of 50% hydrochloric acid. The mixture was extracted with n.hexane (4×50 ml).

The reunited hexane extracts were washed with water till a neutral pH and dried on anhydrous Na$_2$SO$_4$.

The solvent was removed by evaporation at reduced pressure, thereby obtaining 3.5 g of the desired product having the same spectroscopic characteristics (IR and $^1$H-NMR) of the corresponding product described in Example 13 of European application No. 31.041.

EXAMPLE 10

Preparation of 1,1,1-trifluoro-2-chloro-2,4-dibromo-7-methyl-octan-6-ol $$F_3C—\underset{Cl}{\underset{|}{C}}—CH_2—\underset{Br}{\underset{|}{CH}}—CH_2—\underset{Br}{\underset{|}{CH}}—\underset{}{\overset{OH}{\overset{|}{CH}}}—\underset{}{\overset{CH_3}{\overset{|}{CH}}}—CH_3.$$

The product was obtained according to the procedure described in Example 6, starting from 83.5 g of CF$_3$—CClBr$_2$ and 22.8 g 4-hydroxy-5-methyl-hexene-1.

64 g of the desired product were obtained as pale yellow oil (yield 82%, IR consistent with the assigned structure).

EXAMPLE 11

Preparation of 1,1,1-trifluoro-2-chloro-2,4-dibromo-7-methyl-octene-6

$$F_3C—\underset{Cl}{\underset{|}{C}}—CH_2—\underset{Br}{\underset{|}{CH}}—CH_2—CH=C\overset{\diagup CH_3}{\diagdown CH_3}.$$

Into a 500 ml flask equipped with stirrer, thermometer, reflux condenser and dripping funnel, there were introduced 40 g of P$_2$O$_5$ under 250 ml of anhydrous benzene.

The mixture was vigorously stirred and to it there were added dropwise 64 g of the product obtained as in Example 10. The mixture heated up spontaneously to 35° C.

One hour thereafter the reaction mixture was cooled at about 0°–5° C. by an external ice-water bath.

To the reaction mixture, 100 ml of distilled water were added slowly and dropwise so as to keep the internal temperature below 15° C.

The organic layer was then separated and the aqueous layer was extracted with diethylether (2×100 ml).

The reunited organic layers were washed with 5% NaHCO₃ solution (2×100 ml) and with water (2×100 ml) and dried on anhydrous Na₂SO₄.

The solvents were then removed by evaporation at reduced pressure and the residue (59.5 g) was chromatographed on silica gel (eluent n.hexane-ethyl acetate in the ratio 99.5:0.5).

Thereby were obtained 23.1 g of the desired product as oil (IR consistent with the assigned structure, $\nu(C=C)$ at 1670 cm$^{-1}$).

EXAMPLE 12

Preparation of 2,2-dimethyl-3-(2,4-dibromo-4-chloro-5,5,5-trifluoropentyl)-cyclopropanecarboxylic acid ethyl ester

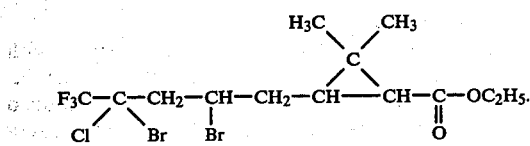

The product was obtained by operating according to the procedure described in Example 8, starting from 11.2 g of 1,1,1-trifluoro-2-chloro-2,4-dibromo-7-methyloctene-6 (see Example 11) and 20.6 g of ethyl diazoacetate.

5.5 g of the desired product were obtained as oil (IR consistent with the assigned structure, $\nu(C=O)=1725$ cm$^{-1}$).

EXAMPLE 13

Preparation of 2,2-dimethyl-3-(4-chloro-5,5,5-trifluoro-1,3-pentadienyl)-cis,trans-cyclopropanecarboxylic acid ethyl ester

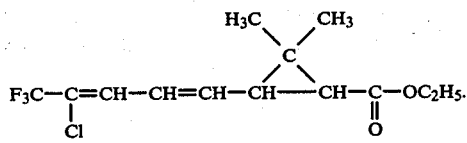

The product was prepared by operating according to the procedure described in Example 9, starting from 4.6 g of the cyclopropanecarboxylate of Example 12 (triethylamine was used as a base instead of diisopropylamine).

1.5 g of the desired product were obtained (¹H-NMR consistent with the assigned structure).

IR: significant bands at 1725, 1640 and 1615 cm$^{-1}$.
¹⁹F-NMR (CDCl₃, CFCl₃) singlet at 69.5 ppm.

What we claim is:
1. A process for the preparation of compounds of general formula:

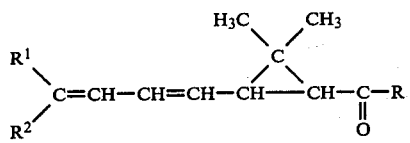

wherein:
R¹ represents F, Cl, Br or CF₃:
R² represents F, Cl or Br;
R represents C₁–C₄ alkoxy;
comprising reacting a haloalkane of formula:

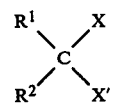

wherein X and X', either equal to or different from each other, represent either a chlorine or a bromine atom, in an inert solvent and in the presence of an organic peroxide or of a Redox-transfer system, with 4-hydroxy-5-methylhexene-1 of formula:

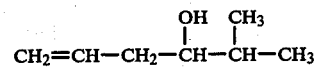

in order to obtain a compound of formula:

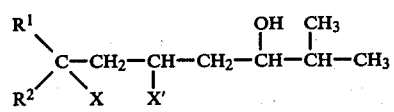

and said compound of formula C is then dehydrated in the presence of P₂O₅ in a suitable solvent or in the presence of strong acids, thus yielding a compound of formula:

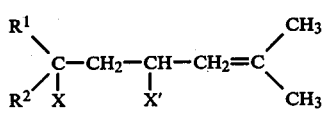

which compound of formula D is made to react with a diazoacetate of formula:

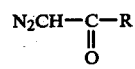

in an inert solvent and in the presence of a catalyttic system consisting of either palladium or rhodium salts or of copper salts in the presence of metal copper, in order to obtain a compound of the formula:

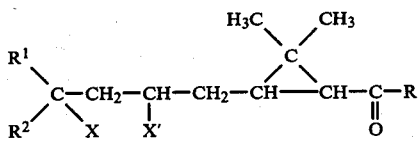

which compound of formula F is finally dehydrohalogenated losing 2 mols of halogenhydric acid (HX and HX') in an inert solvent and in the presence of an at least bimolecular amount of a halogenhydric acid-accepting base.

2. Process according to claim 1, wherein the haloalkane of formula A is a compound selected from the group consisting of:

$CF_3-CFBr_2$, $CF_3-CFCl_2$, $CF_3-CCl_3$, $CF_3-CClBr_2$, $CCl_4$, $CBr_4$ and $CF_2Br_2$.

3. Process according to claim 1, wherein the reaction between the haloalkane A and the alkene B is carried out by using benzoyl peroxide as catalyst.

4. Process according to claim 1, wherein the reaction between the haloalkane A and the alkene B is carried out by using CuCl and triethanol-amine as catalyst.

5. Process according to claim 1, wherein the dehydration of compound C is carried out in anhydrous benzene or in methylene-chloride in the presence of $P_2O_5$.

6. Process according to claim 1, wherein the reaction between compound D and the diazoacetate E is carried out by using, as catalyst, rhodium acetate of formula:

$Rh_2(CH_3COO)_4$.

7. Process according to claim 1, wherein the reaction between compound D and the diazoacetate E is carried out by using copper and copper-sulphate as catalyst.

8. Process according to claim 1, wherein the dehydrohalogenation of compound F is carried out in dimethylformamide in the presence of triethylamine or of diisopropylamine.

* * * * *